United States Patent
Shaw et al.

(10) Patent No.: US 10,463,738 B2
(45) Date of Patent: *Nov. 5, 2019

(54) ORAL COMPOSITION FOR DELIVERY OF DRUGS AND OTHER SUBSTANCES

(71) Applicant: Avanti Polar Lipids, Inc., Alabaster, AL (US)

(72) Inventors: Walter A Shaw, Birmingham, AL (US); Stephen W Burgess, Chelsea, AL (US); Shengrong Li, Birmingham, AL (US)

(73) Assignee: Avanti Polar Lipids, Inc., Alabaster, AL (US)

( * ) Notice: Subject to any disclaimer, the term of this patent is extended or adjusted under 35 U.S.C. 154(b) by 42 days.

This patent is subject to a terminal disclaimer.

(21) Appl. No.: 15/807,389

(22) Filed: Nov. 8, 2017

(65) Prior Publication Data

US 2018/0064813 A1 Mar. 8, 2018

Related U.S. Application Data

(63) Continuation of application No. 14/822,289, filed on Aug. 10, 2015, now Pat. No. 9,872,908.

(60) Provisional application No. 62/035,393, filed on Aug. 9, 2014.

(51) Int. Cl.
| | |
|---|---|
| *A61K 47/24* | (2006.01) |
| *A61K 31/05* | (2006.01) |
| *A61K 31/661* | (2006.01) |
| *A61K 31/12* | (2006.01) |
| *A61K 47/10* | (2017.01) |
| *A61K 9/16* | (2006.01) |
| *A61K 47/12* | (2006.01) |
| *A61K 9/00* | (2006.01) |

(52) U.S. Cl.
CPC ............ *A61K 47/24* (2013.01); *A61K 9/1617* (2013.01); *A61K 31/05* (2013.01); *A61K 31/12* (2013.01); *A61K 31/661* (2013.01); *A61K 47/10* (2013.01); *A61K 47/12* (2013.01); *A61K 9/0095* (2013.01)

(58) Field of Classification Search
CPC ...... A61K 47/24; A61K 9/1617; A61K 31/05; A61K 31/12; A61K 31/661; A61K 47/10; A61K 47/12; A61K 9/0095
USPC .......................................................... 514/679
See application file for complete search history.

(56) References Cited

U.S. PATENT DOCUMENTS

| | | | |
|---|---|---|---|
| 4,619,794 A | 10/1986 | Hauser | |
| 4,874,795 A | 10/1989 | Yesair | |
| 9,872,908 B2 * | 1/2018 | Shaw | ................... A61K 31/05 |
| 2003/0077297 A1 | 4/2003 | Chen | |
| 2003/0235595 A1 | 12/2003 | Chen et al. | |

FOREIGN PATENT DOCUMENTS

| | | |
|---|---|---|
| EP | 0102324 | 3/1984 |
| EP | 2526971 | 11/2012 |
| JP | 2014-516969 | 7/2014 |
| WO | 2012/160203 | 11/2012 |

OTHER PUBLICATIONS

Madalinska, K "Extended European Search Report—European application No. 15832041.6" European patent office; dated March 18, 2016; pp. 1-8.
Yodborovsky, Yivgenia, "Israel Office Action—Israel Application No. 250394" Israel Patent Office; dated May 15, 2019; pp. 1-3.
Wang, Fangfei, "China First Office Action—China Application No. 201580049486.0" China Patent Office; dated Apr. 1, 2019; pp. 1-10.
"Japan Office Action—Japan Application No. 2017-527546" Japan Patent Office; dated Jul. 30, 2019; pp. 1-6.

* cited by examiner

*Primary Examiner* — Yevgeny Valenrod
(74) *Attorney, Agent, or Firm* — Thomas G. Peterson; Maynard Cooper & Gale

(57) ABSTRACT

The present disclosure provides for a composition which may be used for the solublization of an agent or the oral administration of an agent, the composition comprising, a lyosphosphatidyl compound and at least one of a monoglyceride and a free fatty acid. In certain embodiments, the composition comprises a lyosphosphatidyl compound, a monoglyceride and a free fatty acid. In certain embodiments, the composition comprises an agent, a lyosphosphatidyl compound, a monoglyceride and a free fatty acid.

20 Claims, 5 Drawing Sheets

ORAL COMPOSITION FOR DELIVERY OF DRUGS AND OTHER SUBSTANCES

CROSS-REFERENCE TO RELATED APPLICATIONS

This application is a continuation of U.S. patent application Ser. No. 14/822,289, filed Aug. 10, 2015. U.S. patent application Ser. No. 14/822,289 cites the priority of U.S. provisional patent application No. 62/035,393, tiled Aug. 9, 2014 (expired).

BACKGROUND

The delivery of active agents, such as therapeutics, to the body can be problematic. With orally administered drugs, the amount of the agents that reaches the systemic circulation can be much less than the dose administered. Furthermore, orally delivered drugs often have poor bioavailability due to a variety of factors (for example, poor solubility in the gut, degradation and the like). Many attempts to circumvent this problem have been attempted. However, the art remains in need of improved compositions for the oral delivery of agents. The present disclosure provides a novel composition for superior solublization of active agents and for formulating active agents for oral administration.

SUMMARY OF THE DISCLOSURE

The present disclosure provides a composition for the solublization of agents. The present disclosure also provides a composition for the oral delivery of agents.

In a general aspect, the present disclosure provides for a composition comprising an agent, a lysophosphatidyl compound and at least one of a monoglyceride and a free fatty acid.

In a first aspect, the composition comprises a lysophosphatidyl compound of the formula I and at least one a monoglyceride of the general formula IV, a free fatty acid of the general formula V, or a combination of a monoglyceride of the general formula IV and a free fatty acid of the general formula V.

In a second aspect, the composition comprises, a lysophosphatidyl compound of the formula I and at least one of a monoglyceride of the general formula IVA, a free fatty acid of the general formula V, or a combination of a monoglyceride of the general formula IVA and a free fatty acid of the general formula V.

In a third aspect, the composition comprises a lysophosphatidyl compound of the formula I and at least one of a monoglyceride of the general formula IVC, a free fatty acid of the general formula VA, or a combination of a monoglyceride of the general formula IVC and a free fatty acid of the general formula VA.

In a fourth aspect, the composition comprises a lysophosphatidyl compound of the formula II and at least one a monoglyceride of the general formula IV, a free fatty acid of the general formula V, or a combination of a monoglyceride of the general formula IV and a free fatty acid of the general formula V.

In a fifth aspect, the composition comprises a lysophosphatidyl compound of the, formula II and at least one of a monoglyceride of the general formula IVA, a free fatty acid of the general formula V, or a combination of a monoglyceride of the general formula IVA and a free fatty acid of the general formula V.

In a sixth aspect, the composition comprises a lysophosphatidyl compound of the formula II and at least one of a monoglyceride of the general formula IVC, a free fatty acid of the general formula VA, or a combination of a monoglyceride of the general formula IVC and a free fatty acid of the general formula VA.

In a seventh aspect, the composition comprises a lysophosphatidyl compound of the formula III and at least one a monoglyceride of the general formula IV, a free fatty acid of the general formula V, or a combination of a monoglyceride of the general formula IV and a free fatty acid of the general formula V.

In an eighth aspect, the composition comprises a lysophosphatidyl compound of the formula III and at least one of a monoglyceride of the general formula IVA, a free fatty acid of the general formula V, or a combination of a monoglyceride of the general formula IVA and a free fatty acid of the general formula V.

In a ninth aspect, the composition comprises a lysophosphatidyl compound of the formula III and at least one of a monoglyceride of the general formula IVC, a free fatty acid of the general formula VA, or a combination of a monoglyceride of the general formula IVC and a free fatty acid of the general formula VA.

In a tenth aspect, the composition comprises a lysophosphatidyl compound of the formula I, at least one lysophosphatidyl compound of the formula II or III, and at least one a monoglyceride of the general formula IV, a free fatty acid of the general formula V, or a combination of a monoglyceride of the general formula IV and a free fatty acid of the general formula V.

In an eleventh aspect, the composition comprises a lysophosphatidyl compound of the formula I, at least one lysophosphatidyl compound of the formula II or III, and at least one of a monoglyceride of the general formula IVA, a free fatty acid of the general formula V, or a combination of a monoglyceride of the general formula IVA and a free fatty acid of the general formula V.

In a twelfth aspect, the composition comprises a lysophosphatidyl compound of the formula I, at least one lysophosphatidyl compound of the formula II or III, and at least one of a monoglyceride of the general formula IVC, a free fatty acid of the general formula VA, or, a combination of a monoglyceride of the general formula IVC and a free fatty acid of the general formula VA.

In a thirteenth aspect, the composition comprises a lysophosphatidyl compound of the formula IJ, a monoglyceride of the general formula IVC and a free fatty acid of the general formula VA.

In a fourteenth aspect, the composition comprises a lysophosphatidyl compound of the formula IID, a monoglyceride of the general formula IVC and a free fatty acid of the general formula VA.

In a fifteenth aspect, the composition comprises a lysophosphatidyl compound of the formula IIIC, a monoglyceride of the general formula IVC and a free fatty acid of the general formula VA.

In any of the foregoing aspects, the composition is in the form of a eutectic.

In any of the foregoing aspects, the composition is useful for solubilizing an agent. In one embodiment, the agent is one that exhibits poor aqueous solubility. In another embodiment, the agent is one at which the dose strength required for treatment of a subject is not soluble in 100 ml of aqueous solution over a pH range of 1 to 7. In another embodiment, the agent is one at which the dose strength required for treatment of a subject is not soluble in 250 ml of aqueous solution over a pH range of 1 to 7. In another embodiment, the agent is a BCS class II or IV agent. In another, embodiment the compounds is a BCS class III compound.

In any of the foregoing aspects, the composition further comprises an agent, wherein the agent is solubilized in the composition. In one embodiment, the composition and the agent form a eutectic. In one embodiment, the agent is one that exhibits poor aqueous solubility. In another embodiment, the agent is one at which the dose strength required for treatment of a subject is not soluble in 100 ml of aqueous solution over a pH range of 1 to 7. In another embodiment, the agent is one at which the dose strength required for treatment of a subject is not soluble in 250 ml of aqueous solution over a pH range of 1 to 7. In another embodiment, the agent is a BCS class II or IV agent. In another embodiment the compounds is a BCS class III compound.

In any of the foregoing aspects, the composition further comprises an agent and the composition is used for oral delivery of the agent to a subject. In one embodiment, the composition and the agent form a eutectic. In one embodiment, the agent is one that exhibits poor aqueous solubility. In another embodiment, the agent is one at which the dose strength required for treatment of a subject is not soluble in 100 ml of aqueous solution over a pH range of 1 to 7. In another embodiment, the agent is one at which the dose strength required for treatment of a subject is not soluble in 250 ml of aqueous solution over a pH range of 1 to 7. In another embodiment, the agent is a BCS class II or IV agent. In another embodiment the compounds is a BCS class III compound.

DETAILED DESCRIPTION

Figure 1:
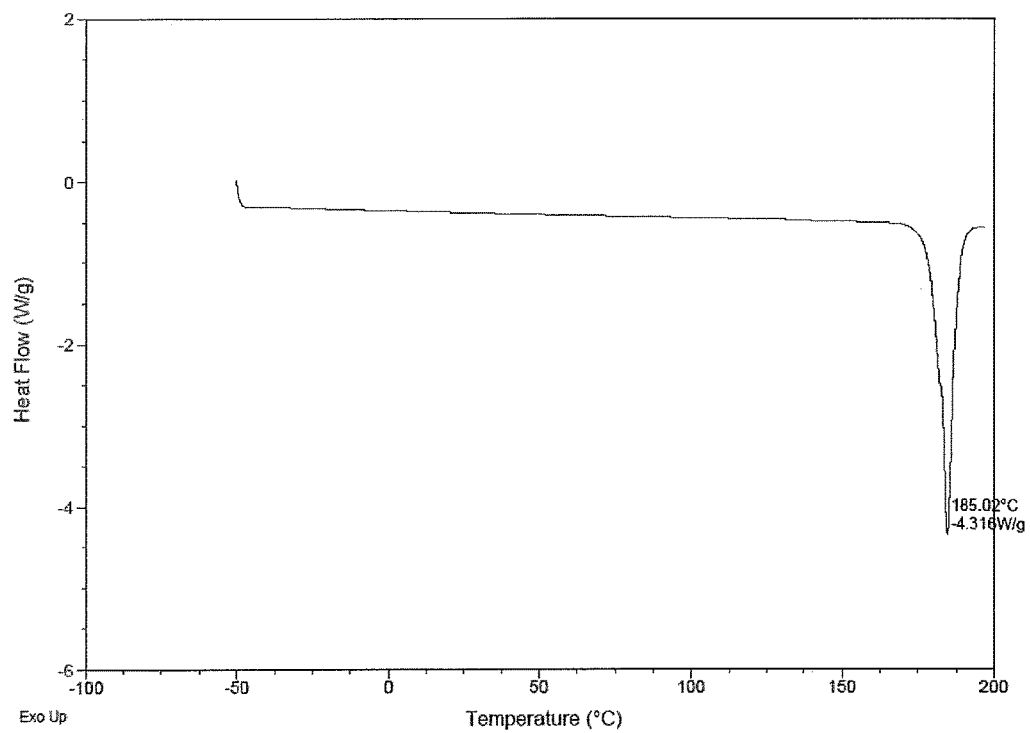
FIG. 1 shows differential scanning calorimetry of a sample of curcumin.

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In its most general embodiment, the present disclosure provides a composition suitable for solubilizing an agent comprising a lysophosphatidyl compound of the general formula I, II or III, a monoglyceride of the formula IV and a free fatty acid of the formula V.

Lysophosphatidyl Compounds

In one embodiment of the foregoing composition, the lysophosphatidyl compound has the general formula I:

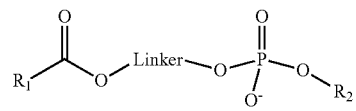

wherein, $R_1$ is a saturated or unsaturated carbon chain;

$R_2$ is H, substituted or unsubstituted acyl, substituted or unsubstituted alkyl, substituted or unsubstituted aryl, substituted or unsubstituted alkene, substituted or unsubstituted alkyne or an amino acid moeity; and, Linker is a Linking Portion.

As stated above, $R_1$ is a saturated or unsaturated carbon chain. In one embodiment, $R_1$ is a saturated carbon chain. In another embodiment, $R_1$ is an unsaturated carbon chain; when $R_1$ is an unsaturated carbon chain, the carbon chain may contain from 1 to 6, from 1 to 4 or from 1 to 3 double or triple bonds. In one embodiment, $R_1$ is an unsaturated carbon chain; containing from 1 to 6, from 1 to 4 or from 1 to 3 double bonds. Such unsaturated carbon chains may be present in the cis or trans configuration, or a mixture of cis and trans configuration.

In another embodiment, $R_1$ is a carbon chain up to 5 carbons in length, a carbon chain from 6 to 12 carbons in length, a carbon chain from 13-21 carbons in length and a carbon chain greater than 22 carbons in length. In a particular aspect, $R_1$ is a carbon chain from 13 to 21 carbons in length. Such carbon chain, regardless of the length, includes both even and odd chain lengths and may be saturated or unsaturated; in one embodiment, the carbon chain is saturated. In another embodiment, $R_1$ is a carbon chain of 3, 4, 5, 6, 7, 8, 9, 10, 11, 12, 13, 14, 15, 18, 19, 20, 21, 22, 23, 24, 25, 26, 27, 28, 29 or 30 or more carbons, which are saturated or unsaturated. In another embodiment, $R_1$ is a carbon chain of 3, 4, 5, 6, 7, 8, 9, 10, 11, 12, 13, 14, 15, 16, 17, 18, 19, 20 or 21 carbons, which are saturated or unsaturated. In another embodiment, $R_1$ is a carbon chain of 10, 11, 12, 13, 14, 15, 16, 17, 18, 19, 20 or 21 carbons, which are saturated or unsaturated. In another embodiment, $R_1$ is a carbon chain of 12, 13, 14, 15 or 16, carbons, which are saturated or unsaturated. In another embodiment, $R_1$ is a carbon chain of 13 carbons, which is saturated.

Non-limiting exemplary lysophosphatidyl compounds for use with the present invention include lauroyl-lysophosphatidyl compounds, myristoyllysophosphatidyl compounds, palmitoyl-lysophosphatidyl compounds, stearoyl-lysophosphatidyl compounds, arachidoyl-lysophosphatidyl compounds, oleoyl-lysophosphatidyl compounds, linoleoyllysophosphatidyl compounds, linolenoyl-lysophosphatidyl compounds and erucoyl lysophosphatidyl compounds.

In one embodiment, $R_2$ is a substituted alkyl chain. In one embodiment, $R_2$ is a substituted alkyl chain from 1 to 10 carbons. In one embodiment, $R_2$ is a substituted alkyl chain, for example a substituted alkyl chain from 1 to 10 carbons, wherein the alkyl chain is substituted by one or more, 1 to 5 or 1 to 2 hydroxy groups, substituted N groups or $NH_3$ groups. In a particular embodiment, the substituted N group is substituted by 1 to 3 C1-C6 alkyl groups. In another embodiment, $R_2$ is $-(CH_2)_2-(N)(CH_3)_3$, $-CH_2-CH(OH)-CH_2-CH(OH)$ or $(CH_2)_2-NH_3$. In one embodiment, $R_2$ does not contain a N group. In one embodiment, $R_2$ is not $-(CH_2)_2-(N)(CH_3)_3$.

In one embodiment, the $R_2$ group is an amino acid moiety of the formula —$CH_2$—$CH(R_3)$—$C$=$O(O^-)$, where $R_3$ is a side chain of a naturally occurring or non-naturally occurring amino acid. In a particular embodiment, $R_3$ is —$NH_3$.

In one aspect of the foregoing, the linker is a non-immunogenic, hydrophilic polymer. Representative hydrophilic polymers include, but are not limited to, linear or branched poly(dextran), linear or branched poly(cellulose), linear and branched poly(ethylene glycol), linear and branched poly(alkylene oxide), linear and branched polyvinyl pyrrolidone), linear and branched polyvinyl alcohol), linear and branched polyoxazoline, linear and branched poly(acryloylmorpholine), and derivatives thereof. In one aspect of the foregoing, the linker is linear poly(ethylene glycol). In any of the foregoing, the repeating units of the polymer may vary from 1 to 50, more particularly from 1 to 25, from 1 to 15, from 1 to 8 or from 1-3.

In one aspect of the foregoing, the linker is a glycerol moiety or a substituted or unsubstituted alkyl chain and the lysophosphatidyl compound has a structure of the general formula IA or IB.

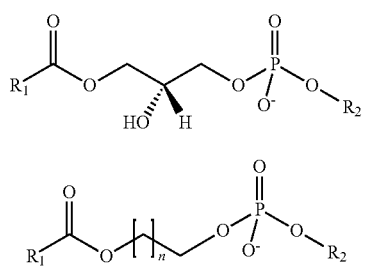

IA

IB

Wherein $R_1$ and $R_2$ are as defined above and n is from 1 to 20, 1 to 10 or 1 to 6. In a particular aspect, n is 1 to 6 1 to 4 or 1 to 2 and the alkyl chain is an unsubstituted alkyl chain.

In one embodiment, the lysophosphatidyl compound is a lysophosphatidylglycerol. In another aspect, the lysophosphatidylglycerol is 1-myristoyl-2-hydroxy-sn-glycero-3-phospho-(1'-rac-glycerol). Representative lysophosphatidyl glycerol compounds include those shown below IC to IE, wherein $R_1$ and n are as defined above.

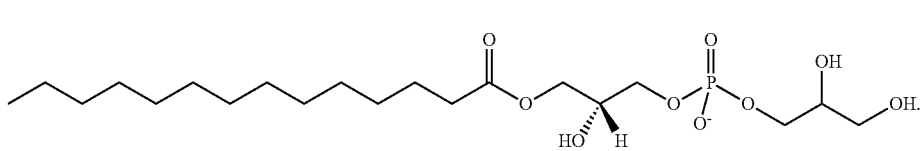

IC

ID

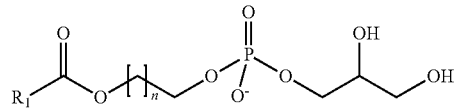

IE

In a particular embodiment, $R_1$ is a saturated carbon chain of 13 carbons in length.

In a particular embodiment, the lysophosphatidyl compound has the structure IJ:

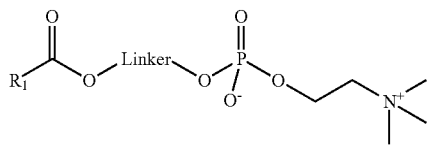

IJ

In one embodiment, the lysophosphatidyl compound is a lysophosphatidylcholine. In another aspect, the lysophosphatidylcholine is 1-myristoyl-2-hydroxy-sn-glycero-3-phosphocholine. Representative lysophosphatidylcholine compounds include those shown below IF and IH, wherein $R_1$ and n are as defined above.

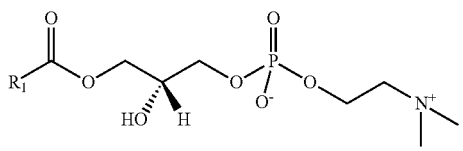

IF

IG

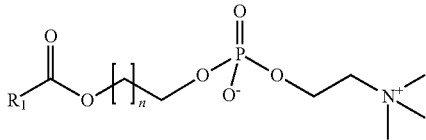

IH

In a particular embodiment, $R_1$ is a saturated carbon chain of 13 carbons in length and the compound has the structure IK

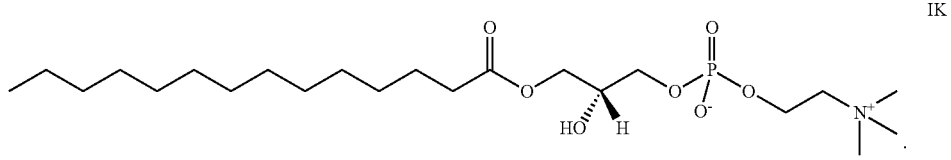 [SMILES: CCCCCCCCCCCCCC(=O)OC[C@@H](O)COP(=O)([O-])OCC[N+](C)(C)C]

IK

In another embodiment of the foregoing composition, the lysophosphatidyl compound has the general formula II:

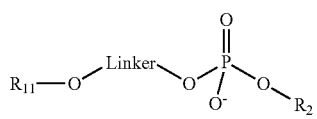

II wherein,
$R_2$ is as defined above in the general formula I;
$R_{11}$ is a saturated or unsaturated carbon chain; and
Linker is a Linking Portion.

As stated above, $R_{11}$ is a saturated or unsaturated carbon chain. In one embodiment, $R_{11}$ is a saturated carbon chain. In another embodiment, $R_{11}$ is an unsaturated carbon chain; when $R_{11}$ is an unsaturated carbon chain, the carbon chain may contain from 1 to 6, from 1 to 4 or from 1 to 3 double or triple bonds. In one embodiment, $R_{11}$ is an unsaturated carbon chain; containing from 1 to 6, from 1 to 4 or from 1 to 3 double bonds. Such unsaturated carbon chains may be present in the cis or trans configuration, or a mixture of cis and trans configuration.

In another embodiment, $R_{11}$ is a carbon chain up to 5 carbons in length, a carbon chain from 6 to 12 carbons in length, a carbon chain from 13-21 carbons in length and a carbon chain greater than 22 carbons in length. In a particular aspect, $R_{11}$ is a carbon chain from 13 to 21 carbons in length. Such carbon chain, regardless of the length, includes both even and odd chain lengths and may be saturated or unsaturated; in one embodiment, the carbon chain is saturated. In another embodiment, $R_{11}$ is a carbon chain of 3, 4, 5, 6, 7, 8, 9, 10, 11, 12, 13, 14, 15, 16, 17, 18, 19, 20, 21, 22, 23, 24, 25, 26, 27, 28, 29 or 30 or more carbons, which are saturated or unsaturated. In another embodiment, $R_{11}$ is a carbon chain of 3, 4, 5, 6, 7, 8, 9, 10, 11, 12, 13, 14, 15, 16, 17, 18, 19, 20 or 21 carbons, which are saturated or unsaturated. In another embodiment, $R_{11}$ is a carbon chain of 10, 11, 12, 13, 14, 15, 16, 17, 18, 19, 20 or 21 carbons, which are saturated or unsaturated. In another embodiment, $R_{11}$ is a carbon chain of 12, 13, 14, 15 or 16, carbons, which are saturated or unsaturated. In another embodiment, $R_{11}$ is a carbon chain of 14 carbons, which is saturated.

In one aspect of the foregoing, the linker is a non-immunogenic, hydrophilic polymer. Representative hydrophilic polymers include, but are not limited to, linear or branched poly(dextran), linear or branched poly(cellulose), linear and branched poly(ethylene glycol), linear and branched poly(alkylene oxide), linear and branched poly(vinyl pyrrolidone), linear and branched polyvinyl alcohol), linear and branched polyoxazoline, linear and branched poly(acryloylmorpholine), and derivatives thereof. In one aspect of the foregoing, the linker is linear poly(ethylene glycol). In any of the foregoing, the repeating units of the polymer may vary from 1 to 50, more particularly from 1 to 25, from 1 to 15, from 1 to 8 or from 1 to 3.

In one aspect of the foregoing, the linker is an alkyl chain and the lysophosphatidyl compound has a structure of the general formula IIA.

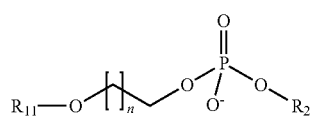

IIA wherein $R_{11}$ and $R_2$ are as defined above and n is from 1 to 20, 1 to 10 or 1 to 6.

In a particular aspect, n is 1 to 6, 1 to 4 or 1 to 2. Compounds of the formula IIA have the advantage that the lysophosphatidyl compounds are not hydrolyzable or are resistant to being hydrolyzed (when compared to compounds of the, general formula I) when administered to subjects, including human subjects.

Representative lysophosphatidyl compounds represented by the general structure IIA include those shown below as IIB and IIC, wherein $R_{11}$ and n are as defined above.

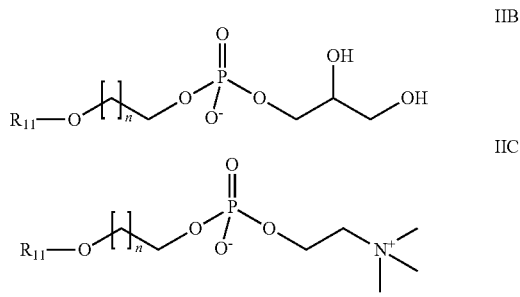

IIB

IIC

In a particular embodiment, $R_{11}$ is a saturated carbon chain of 14 carbons in length and the compound has the structure IID or IIE:

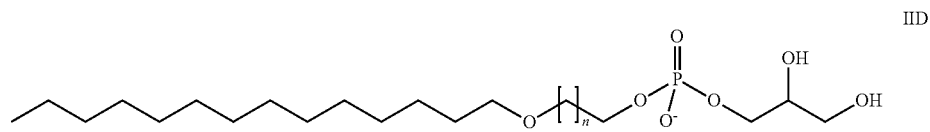

IID

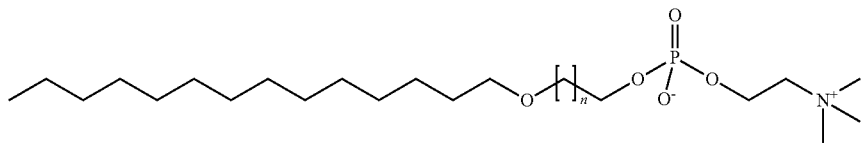
IIE

In another embodiment of the foregoing composition, the lysophosphatidyl compound has the general formula III:

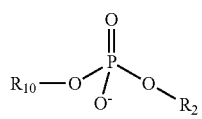
III wherein,
$R_2$ is as defined above in the general formula I; and
$R_{10}$ is a saturated or unsaturated carbon chain.

As stated above, $R_{10}$ is a saturated or unsaturated carbon chain. In one embodiment, $R_{10}$ is a saturated carbon chain. In another embodiment, $R_{10}$ is a an unsaturated carbon chain; when $R_{10}$ is an unsaturated carbon chain, the carbon chain may contain from 1 to 6, from 1 to 4 or from 1 to 3 double or triple bonds. In one embodiment, $R_{10}$ is a an unsaturated carbon chain; containing from 1 to 6, from 1 to 4 or from 1 to 3 double bonds. Such unsaturated carbon chains may be present in the cis or trans configuration, or a mixture of cis and trans configuration.

In another embodiment, $R_{10}$ is a carbon chain up to 5 carbons in length, a carbon chain from 6 to 12 carbons in length, a carbon chain from 13-21 carbons in length and a carbon chain greater than 22 carbons in length. In a particular aspect, $R_{10}$ is a carbon chain from 13 to 21 carbons in length. Such carbon chain, regardless of the length, includes both even and odd chain lengths and may be saturated or unsaturated; in one embodiment, the carbon chain is saturated. In another embodiment, $R_{10}$ is a carbon chain of 3, 4, 5, 6, 7, 8, 9, 10, 11, 12, 13, 14, 15, 16, 17, 18, 19, 20, 21, 22, 23, 24, 25, 26, 27, 28, 29 or 30 or more carbons, which are saturated or unsaturated. In another embodiment, $R_{10}$ is, a carbon chain of 3, 4, 5, 6, 7, 8, 9, 10, 11, 12, 13, 14, 15, 16, 17, 18, 19, 20 or 21 carbons, which are saturated or unsaturated. In another embodiment, $R_{10}$ is a carbon chain of 10, 11, 12, 13, 14, 15, 16, 17, 18 19, 20 or 21 carbons, which are saturated or unsaturated. In another embodiment, $R_{10}$ is a carbon chain of 12, 13, 14, 15 or 16 carbons, which are saturated or unsaturated. In another embodiment, $R_{10}$ is a carbon chain of 14 carbons, which is saturated. Representative lysophosphatidyl compounds represented by the general structure III include those shown below IIIA and IIIB, wherein $R_{10}$ is as defined above.

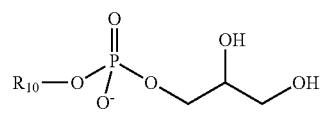
IIIA

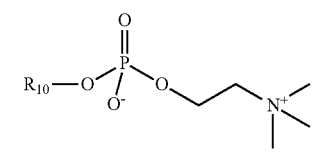
IIIB

In a particular embodiment, $R_{10}$ is a saturated carbon chain of 14 carbons in, length and the compound has the structure IIIC or IIID:

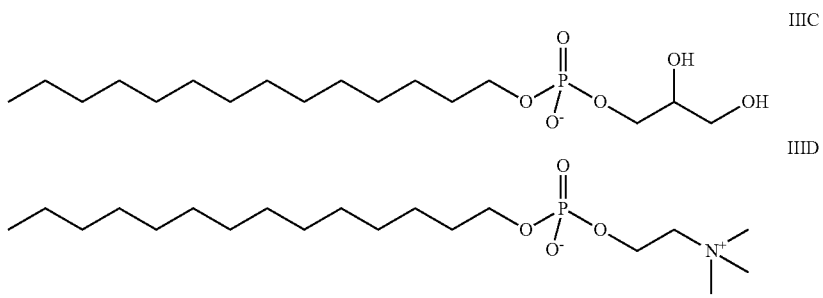
IIIC

IIID

Monoglycerides

Monoglycerides are composed of a glycerol molecule wherein the glycerol molecule has formed an ester bond with exactly one fatty acid molecule. Monoglycerides are also referred to as acylglycerol and monoacylglycerol. Monoglycerides for use in the present disclosure have the general formula IV:

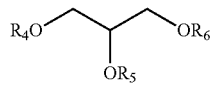
IV wherein: one of $R_4$, $R_5$ and $R_6$ is —C(O)—$R_7$ and the remaining are each independently selected from H or $R_8$, wherein $R_7$ is a saturated or unsaturated carbon chain and $R_8$ is saturated or unsaturated carbon chain from 1 to 10 carbons in length.

As stated above, $R_7$ is a saturated or unsaturated carbon chain. In one embodiment, $R_7$ is a saturated carbon chain. In another embodiment, $R_7$ is an unsaturated carbon chain; when. $R_7$ is an unsaturated carbon chain, the carbon chain may contain from 1 to 6, from 1 to 4 or front 1 to 3 double or triple bonds, in one embodiment, $R_7$ is an unsaturated carbon chain; containing from 1 to 6, from 1 to 4 or from 1 to 3 double bonds. Such unsaturated carbon chains may be present in the cis or trans configuration, or a mixture of cis and trans configuration.

In another embodiment, $R_7$ is a carbon chain up to 5 carbons in length, a carbon chain from 6 to 12 carbons in length, a carbon chain from 13-21 carbons in length and a carbon chain greater than 22 carbons in length. In a particular aspect, $R_7$ is a carbon chain from 13 to 21 carbons in length. Such carbon chain, regardless of the length, includes both even and odd chain lengths and may be saturated or unsaturated; in one embodiment, the carbon chain is saturated. In another embodiment, $R_7$ is a carbon chain of 3, 4, 5, 6, 7, 8, 9, 10, 11, 12, 13, 14, 15, 16, 17, 18, 19, 20, 21, 22, 23, 24, 25, 26, 27, 28, 29 or 30 or more carbons, which are saturated or unsaturated. In another embodiment, $R_7$ is a carbon chain of 3, 4, 5, 6, 7, 8, 9, 10, 11, 12, 13, 14, 15, 16. 17, 18, 19, 20 or 21 carbons, which are saturated or unsaturated. In another embodiment, $R_7$ is a carbon chain of 10, 11, 12, 13, 14, 15, 16, 17, 18, 19, 20 or 21 carbons, which are saturated or unsaturated. In another embodiment, $R_7$ is a carbon chain of 12, 13, 14, 15 or 16, carbons, which are saturated or unsaturated. In another embodiment, $R_7$ is a carbon chain of 13 carbons, which is saturated.

In one embodiment, one of $R_4$, $R_5$ and $R_6$ is —C(O)—$R_7$ and the remaining are H. In one embodiment, one of $R_4$, $R_5$ and $R_6$ is —C(O)—$R_7$ and the remaining are independently H or saturated carbon chain from 1 to 4 or 1 to 2 carbons in length.

A monoacylglycerol is either a 1-monoacylglycerol or a 2-monoacylglycerol, depending on the position of the ester bond on the glycerol moiety. In one embodiment, the monoglyceride is a 1-monoacylglycerol. Representative 1-monoacylglycerols and 2-monoacylglycerols are shown below having the general formula IVA and IVB respectively, wherein $R_7$ is as defined above.

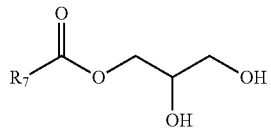

IVA

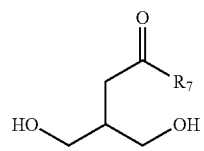

IVB

In a particular embodiment, $R_7$ is a saturated carbon chain of 13 carbons in length. In a particular embodiment, the monoglyceride compound has the structure IVC.

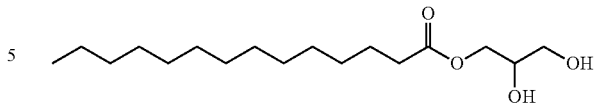

IVC

Non-limiting exemplary monoglyceride compounds for use with the present invention include, but are not limited to, monoglycerides in which the esterified fatty acid is lauric acid, tridecylic acid, myristic acid, pentadecylic acid, palmitic acid, margaric acid, stearic acid, myristoleic acid, palmitoleic acid, sapienic acid, oleic acid, elaidic acid, stearidonic acid, vaccenic acid, linoleic acid, linoelaidic acid, γ-linolenic acid and α-linolenic acid.

Free Fatty Acids

Free fatty acids for use in the present disclosure have the general formula V

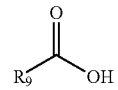

V wherein $R_9$ is a saturated or unsaturated carbon chain.

As stated above, $R_9$ is a saturated or unsaturated carbon chain. In one embodiment, $R_9$ is a saturated carbon chain. In another embodiment, $R_9$ is a an unsaturated carbon chain; when $R_9$ is an unsaturated carbon chain, the carbon chain may contain from 1 to 6, from 1 to 4 or from 1 to 3 double or triple bonds. In one embodiment, $R_9$ is a an unsaturated carbon chain; containing from 1 to 6, from 1 to 4 or from 1 to 3 double bonds. Such unsaturated carbon chains may be present in the cis or trans configuration, or a mixture of cis and trans configuration.

In another embodiment, $R_9$ is a carbon chain up to 5 carbons in length, a carbon chain from 6 to 12 carbons in length, a carbon chain from 13-21 carbons in length and a carbon chain greater than 22 carbons in length. In a particular aspect, $R_9$ is a carbon chain from 13 to 21 carbons in length. Such carbon chain, regardless of the length, includes both even and odd chain lengths and may be saturated or unsaturated; in one embodiment, the carbon chain is saturated. In another embodiment, $R_9$ is a carbon chain of 3, 4, 5, 6, 7, 8, 9, 10, 11, 12, 13, 14, 15, 16, 17, 18, 19, 20, 21, 22, 23, 24, 25, 26, 27, 28, 29 or 30 or more carbons, which are saturated or unsaturated. In another embodiment, $R_9$ is a carbon chain of 3, 4, 5, 6, 7, 8, 9, 10, 11, 12, 13, 14, 15, 16, 17, 18, 1.9, 20 or 21 carbons, which are saturated or unsaturated. In another embodiment, $R_9$ is a carbon chain of 10, 11, 12, 13, 14, 15, 16, 17, 18, 19, 20 or 21 carbons, which are saturated or unsaturated. In another embodiment, $R_9$ is a carbon chain of 12, 13, 14, 15 or 16, carbons, which are saturated or unsaturated. In another embodiment, $R_9$ is a carbon chain of 13 carbons, which is saturated.

In a particular embodiment, $R_9$ is a saturated carbon chain of 13 carbons in length. In one embodiment, the fatty acid compound has the structure VA.

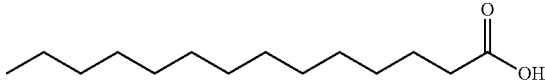

VA

Non-limiting exemplary free fatty acids for use with the present disclosure include, but are not limited to, lauric acid, tridecylic acid, myristic acid, pentadecylic acid, palmitic acid, margaric acid, stearic acid, myristoleic acid, palmitoleic acid, sapienic acid, oleic acid, elaidic acid, stearidonic acid, vaccenic acid, linoleic acid, linoelaidic acid, γ-linolenic acid and α-linolenic acid.

Compositions

In first embodiment, the composition comprises a lysophosphatidyl compound of the formula I and at least one a monoglyceride of the general formula IV, a free fatty acid of the general formula V, or a combination of a monoglyceride of the general formula IV and a free fatty acid of the general formula V.

In a second embodiment, the composition comprises a lysophosphatidyl compound of the formula I and at least one of a monoglyceride of the general formula IVA, a free fatty acid of the general formula V, or a combination of a monoglyceride of the general formula IVA and a free fatty acid of the general formula V.

In a third embodiment, the composition comprises a lysophosphatidyl compound of the formula and at least one of a monoglyceride of the general formula IVC, a free fatty acid of the general formula VA, or a combination of a monoglyceride of the general formula IVC and a free fatty acid of the general formula VA.

In the foregoing first through third embodiments, the lysophosphatidyl compound of the formula I may be a compound of the formula IA or IB or a combination of the foregoing. In the foregoing first through third embodiments, the lysophosphatidyl compound of the formula I may be a compound of the formula IC, ID, IE, IJ, or a combination of the foregoing. Further, in the foregoing first through third embodiments, the lysophosphatidyl compound of the formula I may be a compound of the formula IF, IG, IH, IK or a combination of the foregoing. Further, in the foregoing first through third embodiments, the lysophosphatidyl compound of the formula I may be a compound of the formula IC, ID, IE, IJ, IF, IG, IH, IK or a combination of the foregoing. Further, in the foregoing first through third embodiments, the lysophosphatidyl compound of the formula I may be a compound of the formula. IC, ID, IE, IJ, IH or a combination of the foregoing. Still further, in the foregoing first through third embodiments, the lysophosphatidyl compound of the formula I may be a compound of the formula IJ.

In the foregoing first through third embodiments, the composition comprises, a lysophosphatidyl compound, a monoglyceride and a free fatty acid. In the foregoing first through third embodiments, the alkyl chain of the lysophosphatidyl compound ($R_1$) is of an equal length as the alkyl chains of the free fatty acid ($R_9$) and monoglyceride (one of $R_4$, $R_5$ and $R_6$).

In a fourth embodiment, the composition comprises a lysophosphatidyl compound of the formula II and at least one a monoglyceride of the general formula IV, a free fatty acid of the general formula V, or a combination of a monoglyceride of the general formula IV and a free fatty acid of the general formula V.

In a fifth embodiment, the composition comprises a lysophosphatidyl compound of the formula II and at least one of a monoglyceride of the general formula IVA, a free fatty acid of the general formula V, or a combination of a monoglyceride of the general formula IVA and a free fatty acid of the general formula V.

In a sixth embodiment, the composition comprises a lysophosphatidyl compound of the formula II and at least one of a monoglyceride of the general formula IVC, a free fatty acid of the general formula VA, or a combination of a monoglyceride of the general formula IVC and a free fatty acid of the general formula VA.

In the foregoing fourth through sixth embodiments, the lysophosphatidyl compound of the formula II may be a compound of the formula IIA. Further, in the foregoing fourth through sixth embodiments, the lysophosphatidyl compound of the formula II may be a compound of the formula IIB, IIC or a combination of the foregoing. Still further, in the foregoing fourth through sixth embodiments, the lysophosphatidyl compound of the formula II may be a compound of the formula IID or IIE. Still further, in the foregoing fourth through sixth embodiments, the lysophosphatidyl compound of the formula II may be a compound of the formula IID. Still further, in the foregoing fourth through sixth embodiments, the lysophosphatidyl compound of the formula II may be a compound of the formula IIE.

In the foregoing fourth through sixth embodiments, the composition comprises a lysophosphatidyl compound, a monoglyceride and a free fatty acid. In the foregoing fourth through sixth embodiments, the alkyl chain of the lysophosphatidyl compound ($R_{11}$) is of an equal length as the alkyl chains of the free fatty acid ($R_9$) and monoglyceride (one of $R_4$, $R_5$ and $R_6$).

In a seventh embodiment, the composition comprises a lysophosphatidyl compound of the formula III and at least one a monoglyceride of the general formula IV, a free fatty acid of the general formula V, or a combination of a monoglyceride of the general formula IV and a five fatty acid of the general formula V.

In an eighth embodiment, the composition comprises a lysophosphatidyl compound of the formula III and at least one of a monoglyceride of the general formula IVA, a free fatty acid of the general formula V, or a combination of a monoglyceride of the general formula IVA and a free fatty acid of the general formula V.

In a ninth embodiment, the composition comprises a lysophosphatidyl compound of the formula III and at least one of a monoglyceride of the general formula IVC, a free fatty acid of the general formula VA, or a combination of a monoglyceride of the general formula IVC and a free fatty acid of the general formula VA.

In the foregoing seventh through ninth embodiments, the lysophosphatidyl compound of the formula III may be a compound of the formula IIIA, IIIB or a combination of the foregoing. Further, in the foregoing seventh through ninth embodiments, the lysophosphatidyl compound of the formula III may be a compound of the formula IIIC or IIID. Further, in the foregoing seventh through ninth embodiments, the lysophosphatidyl compound of the formula III may be a compound of the formula IIIC. Further, in the foregoing seventh through ninth embodiments, the lysophosphatidyl compound of the formula III may be a compound of the formula IIID.

In the foregoing seventh through ninth embodiments, the composition comprises a lysophosphatidyl compound, a monoglyceride and a free fatty acid. In the foregoing seventh through ninth embodiments, the alkyl chain of the lysophosphatidyl compound ($R_{10}$) is of an equal length as the alkyl chains of the free fatty acid ($R_9$) and monoglyceride (one of $R_4$, $R_5$ and $R_6$)

In a tenth embodiment, the composition comprises a lysophosphatidyl compound of the formula I, at least one lysophosphatidyl compound of the formula II or III, and at least one a monoglyceride of the general formula IV, a free fatty acid of the general formula V, or a combination of a monoglyceride of the general formula IV and a free fatty acid of the general formula V.

In an eleventh embodiment, the composition comprises a lysophosphatidyl compound of the formula I at least one lysophosphatidyl compound of the formula II or III, and at least one of a monoglyceride of the general formula IVA, a free fatty acid of the general formula V, or a combination of a monoglyceride of the general formula IVA and a free fatty acid of the general formula V.

In a twelfth embodiment, the composition comprises a lysophosphatidyl compound of the formula I at least one lysophosphatidyl compound of the formula II or III, and at least one of a monoglyceride of the general formula IVC, a free fatty acid of the general, formula VA, or a combination of a monoglyceride of the general formula IVC and a free fatty acid of the general formula VA.

In the foregoing tenth through twelfth embodiments, the composition may comprise a lysophosphatidyl compound of the formula I and a lysophosphatidyl compound of the formula II, a lysophosphatidyl compound of the formula I and a lysophosphatidyl compound of the formula III or a lysophosphatidyl compound of the formula I and a lysophosphatidyl compound of the formula II and III.

In the foregoing tenth through twelfth embodiments, the lysophosphatidyl compound of the formula I may be: (i) a compound of the formula IA or IB or a combination of the foregoing; (ii) a compound of the formula IC, ID, IE, IJ, IF, IG, IH, IK or a combination of the foregoing; (iii) a compound of the formula IC, ID, IE, IJ or a combination of the foregoing; (iv) a compound of the formula IF, IG, IH, IK or a combination of the foregoing; or (v) a compound of the formula IJ.

In the foregoing tenth through twelfth embodiments, the lysophosphatidyl compound of the formula II may be: (i) a compound of the formula IIA; (ii) a compound of the formula IIB, IIC or a combination of the foregoing; (iii) a compound of the formula IID or IIE; (iv) a compound of the formula IID; or (v) a compound of the formula IIE In the foregoing tenth through twelfth embodiments, the lysophosphatidyl compound of the formula III may be: (i) a compound of the formula IIIA, IIIB or a combination of the foregoing; (ii) a compound of the formula IIIC or IIID; (iii) a compound of the formula IIIC; or (iv) a compound of the formula IIID.

In the foregoing tenth through twelfth embodiments, the composition comprises a lysophosphatidyl compound of the formula IJ and a lysophosphatidyl compound of the formula IID, a lysophosphatidyl compound of the formula IJ and a lysophosphatidyl compound of the formula IIIC, or a lysophosphatidyl compound of the formula IJ, a lysophosphatidyl compound of the formula IID and a lysophosphatidyl compound of the formula IIIC.

In the foregoing tenth through twelfth embodiments, the composition comprises, at least one lysophosphatidyl compound in the combinations as described above, a monoglyceride and a free fatty acid. In the foregoing tenth through twelfth embodiments, the alkyl chain of the lysophosphatidyl compound ($R_1$, $R_{10}$ or $R_{11}$) is of an equal length as the alkyl chains of the free fatty acid ($R_9$) and monoglyceride (one of $R_4$, $R_5$ and $R_6$)

In a thirteenth embodiment, the composition comprises a lysophosphatidyl compound of the formula IJ, a monoglyceride of the general formula IVC and a free fatty acid of the general formula VA.

In a fourteenth embodiment, the composition comprises a lysophosphatidyl compound of the formula IID, a monoglyceride of the general formula IVC and a free fatty acid of the general formula VA.

In a fifteenth embodiment, the composition comprises a lysophosphatidyl compound of the formula IIIC, a monoglyceride of the general formula IVC and a free fatty acid of the general formula. VA.

In a sixteenth embodiment, the composition comprises a lysophosphatidyl compound of the formula IJ and at least one lysophosphatidyl compound of the formula IID or IIIC, a monoglyceride of the general formula IVC and a free fatty acid of the general formula VA.

In a seventeenth embodiment, the composition comprises a lysophosphatidyl compound of the formula IJ and a lysophosphatidyl compound of the formula IID, a monoglyceride of the general formula IVC and a free fatty acid of the general formula VA.

In an eighteenth embodiment, the composition comprises a lysophosphatidyl compound of the formula IJ and a lysophosphatidyl compound of the formula IIIC, a monoglyceride of the general formula IVC and a free fatty acid of the general formula VA.

In a nineteenth embodiment the composition comprises a lysophosphatidyl compound of the formula IJ and a lysophosphatidyl compound of the formula IID and IIIC, a monoglyceride of the general formula IVC and a free fatty acid of the general formula VA.

In the foregoing first through nineteenth embodiments, the composition may form a eutectic.

Solublization of Agents in Compounds

The composition of the present disclosure is adapted for solublization of agents.

In a twentieth embodiment, the composition further comprises an agent, wherein the agent is solubilized in any one of the compositions of embodiments 1-19 above.

In a twenty-first embodiment, the composition further comprises an agent, wherein the agent is solubilized in composition of embodiment 13 above.

In twenty-second embodiment, the composition further comprises an agent, wherein the agent is solubilized in composition of embodiment 14 above.

In twenty-third embodiment, the composition further comprises an agent, wherein the agent is solubilized in composition of embodiment 15 above.

In twenty-fourth embodiment, the composition further comprises an agent, wherein the agent is solubilized in composition of embodiment 16 above.

In twenty-fifth embodiment, the composition further comprises an agent, wherein the agent is solubilized in composition of embodiment 17 above.

In twenty-sixth embodiment, the composition further comprises an agent, wherein the agent is solubilized in composition of embodiment 18 above.

In twenty-seventh embodiment, the composition further comprises an agent, wherein the agent is solubilized in composition of embodiment 19 above.

In the foregoing twentieth through twenty-seventh embodiments, the agent may be one that exhibits poor aqueous solubility. In the foregoing twentieth through twenty-seventh embodiments, the agent may be one at which the dose strength required for treatment of a subject is not soluble in 100 ml of aqueous solution over a pH range of 1 to 7.

In the foregoing twentieth through twenty-seventh embodiments, the agent may be one at which the dose strength required for treatment of a subject is not soluble in 250 ml of aqueous solution over a pH range of 1 to 7. In the foregoing twentieth through twenty-seventh embodiments, the agent may be a BCS class II or IV agent. In the foregoing twentieth through twenty-seventh embodiments, the agent may be a BCS class III compound. In the foregoing twentieth through twenty-seventh embodiments, the composition and the agent may form a eutectic.

Compounds for Oral Administration of Agents

The composition of the present disclosure is adapted for oral delivery of agents.

In a twenty-eighth embodiment, the composition further comprises an agent, wherein the agent is solubilized in any one of the compositions of embodiments 1-19 above and the composition is used for oral delivery of the agent to a subject.

hi a twenty-ninth embodiment, the composition further comprises an agent, wherein the agent is solubilized in the compositions of embodiment 13 above and the composition is used for oral delivery of the agent to a subject.

In a thirtieth embodiment, the composition further comprises an agent, wherein the agent is solubilized in the compositions of embodiment 14 above and the composition is used for oral delivery of the agent to a subject.

In a thirty-first embodiment, the composition further comprises an agent, wherein the agent is solubilized in the compositions of embodiment 15 above and the composition is used for oral delivery of the agent to a subject.

In a thirty-second embodiment, the composition further comprises an agent, wherein the agent is solubilized in the compositions of embodiment 16 above and the composition is used for oral delivery of the agent to a subject.

In a thirty-third embodiment, the composition further comprises an agent, wherein the agent is solubilized in the compositions of embodiment 17 above and the composition is used for oral delivery of the agent to a subject.

In a thirty-fourth embodiment, the composition further comprises an agent, wherein the agent is solubilized in the compositions of embodiment 18 above and the composition is used for oral delivery of the agent to a subject.

In a thirty-fifth embodiment, the composition further comprises an agent, wherein the agent is solubilized in the compositions of embodiment 19 above and the composition is used for oral delivery of the agent to a subject.

In the foregoing twenty-eighth through thirty-fifth embodiments, the agent may be one that exhibits poor aqueous solubility. In the foregoing twenty-eighth through thirty-fifth embodiments, the agent may be one at which the dose strength required for treatment of a subject is not soluble in 100 ml of aqueous solution over a pH range of 1 to 7. In the foregoing twenty-eighth through thirty-fifth embodiments, the agent may be one at which the dose strength required for treatment of a subject is not soluble in 250 ml of aqueous solution over a pH range of 1 to 7. In the foregoing twenty-eighth through thirty-fifth embodiments, the agent may be a BCS class II or IV agent. In the foregoing twenty-eighth through thirty-fifth embodiments, the agent may be a BCS class III compound. In the foregoing twenty-eighth through thirty-fifth embodiments, the composition and the agent may form a eutectic.

Compositions for the oral delivery of agents may be used in combination with ancillary agents that improve the bioavailability of the composition and/or agent. In one embodiment, the ancillary agent is an inhibitor of a small intestine efflux transporter (i.e., a small intestine efflux inhibitor). Representative small intestine efflux transporters include, but are not limited to, transporters of the ABC family such as MDRI (P-glycoprotein,P-gp, ABCB1), BCRP (ABCG2), and MRP2 (ABCC2). In one embodiment, the small intestine efflux inhibitor is selected from the group consisting of verapamil, cyclosporin A, cyclosporine D, erythromycin, quinine, fluphenazine, reserpine, progesterone, tamoxifen, mitotane, annamycin, biricodar, elacridar, tariquidar and zosuquidar. The ancillary agents may be a part of the composition. The ancillary agent may separate from the composition. In one embodiment, the ancillary agent is administered before a composition of the present disclosure. In one embodiment, the ancillary agent is administered at the same time or after a composition of the present disclosure.

Therefore, in the twenty-eighth through thirty-fifth embodiments, the composition may be administered with an ancillary agent.

Ratios of Components

As discussed above, the free (non-esterified) fatty acids and the esterified fatty acids of the monoglyceride and lysophosphatidyl components may be saturated or unsaturated. If the free fatty acids of the composition are saturated, sufficient quantities of mono-valent and divalent cations may be optionally added to form fatty acid salts. In one embodiment, the cations are present at a molar concentration of approximately one-half of the molar amount of the fatty acid. Suitable cations include sodium and calcium ions. Furthermore the lysophosphatidyl compounds and monoglyceride compounds of the present disclosure may be present as salts as well.

In one embodiment, the free fatty acid and monoglyceride are present in the composition in a molar ratio of between about 2:1 and 1:2 (including any subrange therebetween, such as 1:1). In one embodiment, the free fatty acid and monoglyceride comprise from about 70 mole to 99 mole percent of the composition, with the lysophosphatidyl compound comprising from about 30 mole percent to 1 mole percent of the composition. The above mole percentages are expressed with regard to the lipid components of the composition.

In an exemplary embodiment of the composition the free fatty acid and monoglyceride are present in the composition in a molar ratio of about 2:1 and the lysophosphatidyl compound comprises from about 5 to 20 mole percent. In another exemplary embodiment of the composition the free fatty acid and monoglyceride are present in the composition in a molar ratio of about 2:1 and the lysophosphatidyl compound comprises from about 10 to 18 mole percent. In an exemplary embodiment of the composition the free fatty acid and monoglyceride are of the general formula VA and IVC, respectively, and are present in the composition in a molar ratio of about 2:1 and the lysophosphatidyl compound of the general formula IJ comprises from about 5 to 20 or 10 to 18 mole percent.

In one embodiment, the ratios of the components of the composition are about 1:4:2 lysophosphatidyl compound:monoglyceride:free fatty acid. In another embodiment, the ratios of the components of the composition are about 1:3:3 lysophosphatidyl compound:monoglyceride:free fatty acid. In still another embodiment, the ratios of the components of the composition are about 1:2:4 lysophosphatidyl. compound:monoglyceride:free fatty acid. In another embodiment, the ratios of the components of the composition are about 2:4:2 lysophosphatidyl compound:monoglyceride: free fatty acid.

The foregoing discussion regarding specific ranges of components applies to all of the embodiments described herein. In a specific embodiment, the discussion regarding specific ranges of components applies to first to nineteenth embodiments described above. In a specific embodiment, the discussion regarding specific ranges of components applies to thirteenth to nineteenth embodiments described above. In a specific embodiment, the discussion regarding specific ranges of components applies to the thirteenth embodiments described above. In a specific embodiment, the discussion regarding specific ranges of components applies to the fourteenth embodiments described above. In a specific embodiment, the discussion regarding specific ranges of components applies to the fifteenth embodiments described above. In a specific embodiment, the discussion regarding specific ranges of components applies to the sixteenth embodiments described above. In a specific embodiment, the discussion regarding specific ranges of components applies to the seventeenth embodiments described above. In a specific embodiment, the discussion regarding specific ranges of components applies to the eighteenth embodiments described above. In a specific embodiment, the discussion regarding specific ranges of components applies to the nineteenth embodiments described above.

Agents

The compositions of the present disclosure may be used to provide oral delivery of any agent. In one embodiment, the agent is a therapeutic agent. Such therapeutic agents may be used to treat and/or prevent a variety of disease or conditions, such as but not limited to, cardiac, allergic, infections or cancer related diseases or conditions.

In one embodiment, the agent is fat soluble. In one embodiment, the agent is one that has a low solubility, a low permeability or a combination of the foregoing. In one embodiment, the agent is a BCS class II, class III or class IV compound. Representative BCS class II, class III and IV compounds include, but are not limited to, Acyclovir, Amiloride, Amoxicillin, Atenolol, Atropine, Bisphosphonate, Bidisomide, Captopril, Cefazolin, Cetirizine, Cimetidine, Ciprofloxacin, Cloxacillin, Dicloxacillin, Erythromycin, Famotidine, Amphotericin, Chlorthalidone Chlorothiazide, Colistin, Furosemide, Hydrochlorothiazide, Mebendazole, Methotrexate, and Neomycin. In one embodiment, the agent is curcumin, In one embodiment, the agent may be one that exhibits poor aqueous solubility. In one embodiment, the agent may be one at which the dose strength required for treatment of a subject is not soluble in 100 ml of aqueous solution over a pH range of 1 to 7. In one embodiment, the agent may be one at which the dose strength required for treatment of a subject is not soluble in 250 ml of aqueous solution over a pH range of 1 to 7.

In one embodiment, the composition and the agent form a eutectic.

In one embodiment, the agent is present in a molar concentration of 1:1 with the lysophosphatidyl compound (1:1 agent:lysophosphatidyl compound). In another embodiment, the agent is present in a molar concentration of less than 1:1 with the lysophosphatidyl compound. In still another embodiment, the agent is present in a molar concentration of 0.8:1 with the lysophosphatidyl compound. In still another embodiment, the agent is present in a. molar concentration of 0.5:1 with the lysophosphatidyl compound. In still another embodiment, the agent is present in a molar concentration of 0.1:1 with the lysophosphatidyl compound.

An exemplary formulation includes a composition where the components are present in a molar ratio 1:4:2:1 lysophosphatidyl compound:monoglyceride:free fatty acid: agent. An additional exemplary formulation includes a composition where the components are present in a molar ratio 1:4:2:0.8 lysophosphatidyl compound:monoglyceride:free fatty acid:agent. Still an additional exemplary formulation includes a composition where the components are present in a molar ratio 1:4:2:0.5 lysophosphatidyl compound:monoglyceride:free fatty acid:agent.

In one embodiment, the agent is present in a molar concentration of greater than 1:1 with the lysophospbatidyl compound (agent:lysophosphatidyl compound). In still another embodiment, the agent is present in a molar concentration of 2:1 with the lysophosphatidyl compound. In still another embodiment, the agent is present in a molar concentration of 5:1 with the lysophosphatidyl compound. In still another embodiment, the agent is present in a molar concentration of 10:1 with the lysophosphatidyl compound.

The composition may be any composition described herein. In one embodiment, the composition is a composition of the first to nineteenth embodiments described above. In another embodiment, the composition is a composition of the thirteenth to nineteenth embodiments described above. In a specific embodiment, the composition is a composition of the thirteenth embodiments described above. In a specific embodiment, the composition is a composition of the fourteenth embodiments described above. In a specific embodiment, the composition is a composition of the fifteenth embodiments described above. In a specific embodiment, the composition is a composition of the sixteenth embodiments described above. In a specific embodiment, the composition is a composition of the seventeenth embodiments described above. In a specific embodiment, the composition is a composition of the eighteenth embodiments described above. In a specific embodiment, nineteenth embodiments described above.

Methods of Preparing the Compositions

The compositions of the present disclosure may be prepared by a variety of methods as is known in the art. In one embodiment, the compositions of the present disclosure are prepared by weighing an appropriate amount of the individual components, in powder form, mixing the components together, dissolving the components in an aqueous buffer, sonicating the components and lyophilizing the mixture. In one embodiment, the lipid components of the mixture are present in a ratio 1:4:2 mole percent lysophosphatidyl compound:monoglyceride:free fatty acid. In one embodiment, the sonication step occurs for 30 minutes to 5 hours at a temperature from 50 to 70 degrees.

The resulting lyophilized powder may be administered as a neat powder, in a matrix (for example, an edible wax or the like, or may be mixed with a liquid or food substance. In addition, the composition may be formed into food articles. such as but not limited to, bars, powders, cookies and the like.

EXAMPLES

Compositions of the present disclosure containing lysophosphatidylglycerol (FIGS. 2-3) were prepare by weighing an appropriate amount of the individual components in powder form (lysophosphatidyl compound of the formula IJ; monoglyceride of the formula IVC; and free fatty acid of the formula VA) along with curcumin and mixing the components together. The resulting composition was solubilized in water and sonicated for 60 minutes at 60 degrees. The resulting mixture was lyophilized to powder form.

Compositions containing lysophosphatidylcholine (lysophosphatidyl compound of the formula IK; monoglyceride of the formula IVC; and free fatty acid of the formula VA) (FIGS. 4 and 5) were prepared in the same manner.

In the following examples, the components of the mixture are present in a ratio 1:4:2:0.8 mole percent lysophosphatidyl compound:monoglyceride:free fatty acid:curcumin.

The compositions were subject to differential scanning calorimetry. The results are shown in FIGS. 1-5

Figure 2:
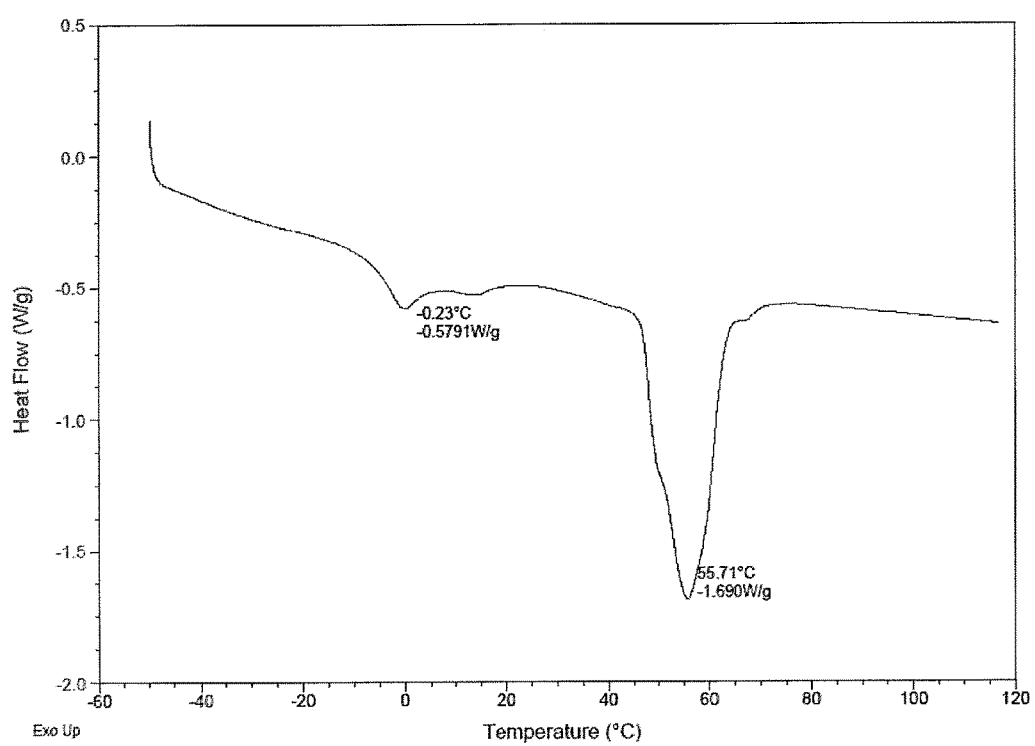
FIG. 2 shows differential scanning calorimetry of a lipid mixture comprising lysophosphatidylglycerol (14:0), monoglyceride (14:0) and fatty acid (14:0).
Figure 3:
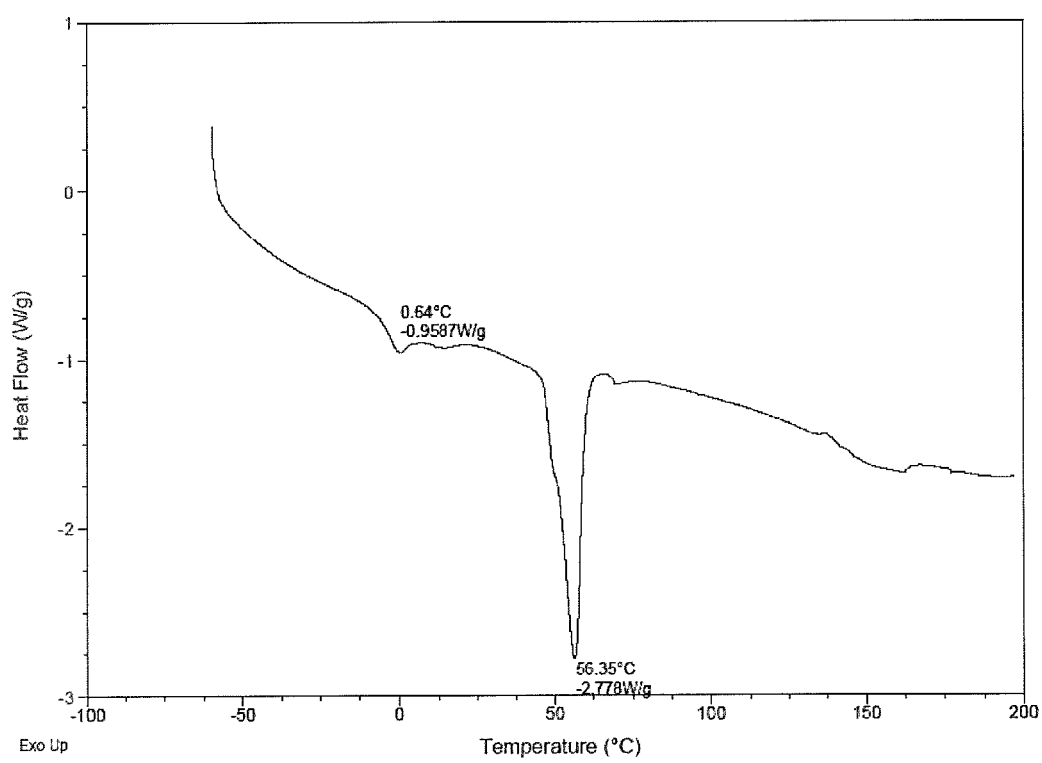
FIG. 3 shows differential scanning calorimetry of a mixture of curcumin and a lipid mixture comprising lysophosphatidylglycerol (14:0), monoglyceride (14:0) and fatty acid (14:0).

FIG. 1 shows differential scanning calorimetry of a sample of curcumin, showing a phase transition at 185.12 degrees C. FIG. 2 shows differential scanning calorimetry of a lipid mixture comprising lysophosphatidylglycerol (14:0), monoglyceride (14:0) and fatty acid (14:0) (molar ratio 1:4:2) showing a phase transition at 55.71 degrees C. FIG. 3 shows differential scanning calorimetry of a mixture of curcumin and a lipid mixture comprising lysophosphatidylglycerol (14:0), monoglyceride (14:0) and fatty acid (14:0) (molar ratio 1:4:2) showing a single phase transition at 56.27 degrees C. The single phase transition of the mixture indicates the composition is a eutectic.

Figure 4:
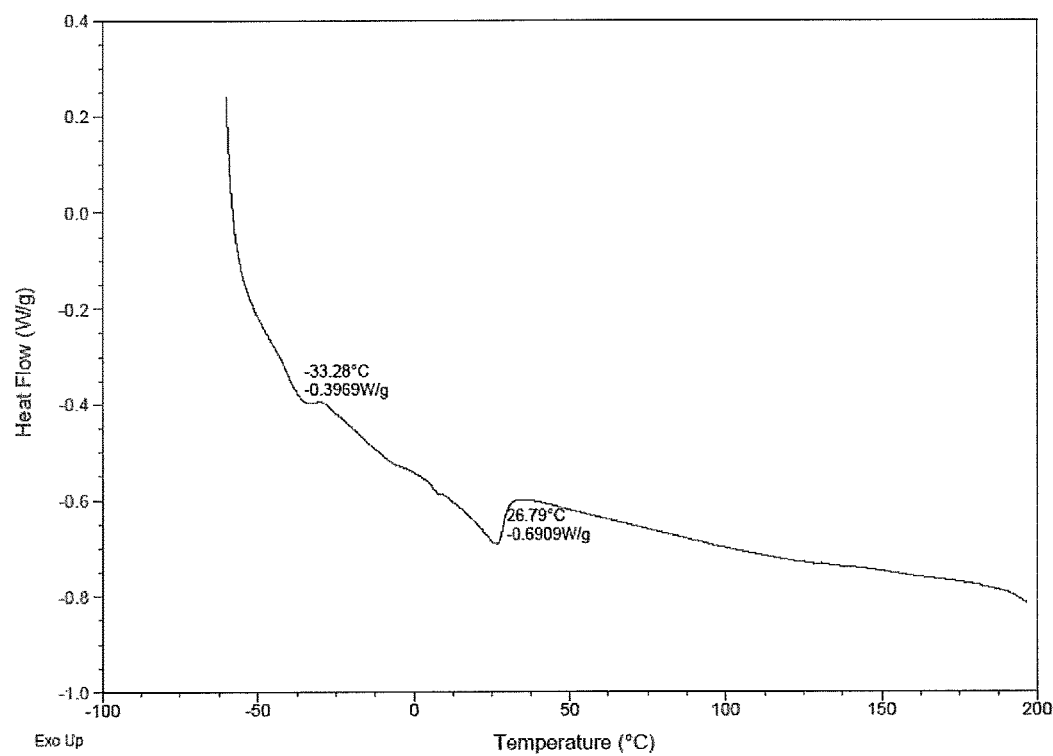
FIG. 4 shows differential scanning calorimetry of a lipid mixture comprising lysophosphatidylcholine (14:0), monoglyceride (14:0) and fatty acid (14:0).
Figure 5:
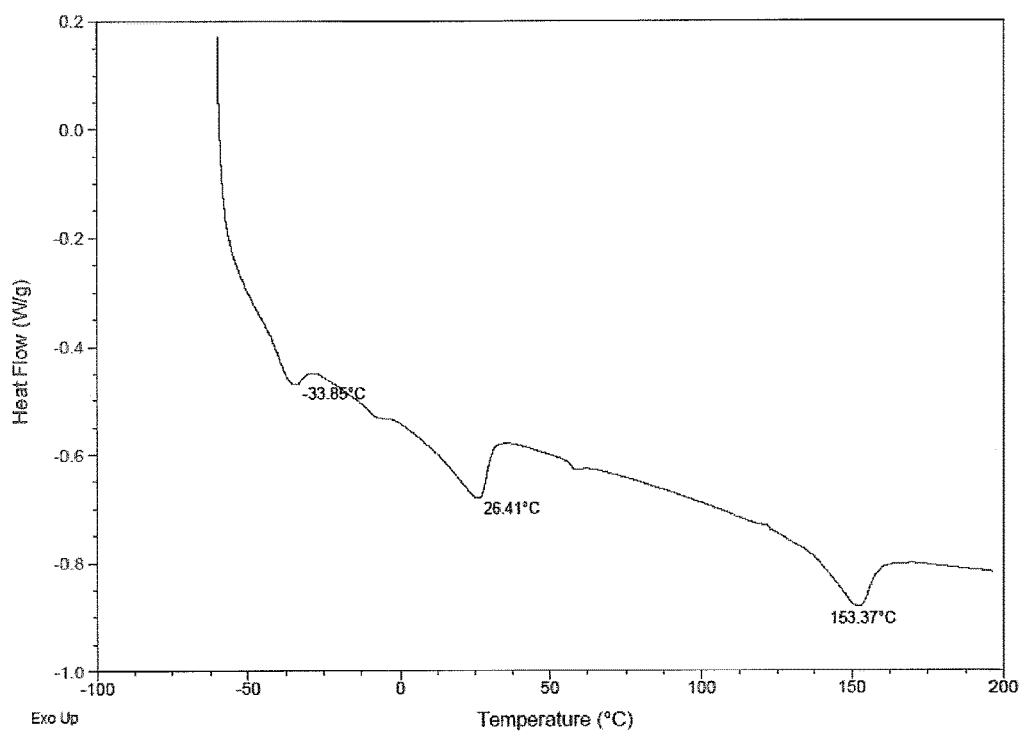
FIG. 5 shows differential scanning calorimetry of a mixture of curcumin and a lipid mixture comprising lysophosphatidylcholine (14:0), monoglyceride (14:0) and fatty acid (14:0).

FIG. 4 shows differential scanning calorimetry of a lipid mixture comprising lysophosphatidylcholine (14:0), monoglyceride (14:0) and fatty acid (14:0) (molar ratio 1:4:2) showing a phase transition at 26.74 degrees C. FIG. 5 shows differential scanning calorimetry of a mixture of curcumin and a lipid mixture comprising lysophosphatidylcholine (14:0), monoglyceride (14:0) and fatty acid (14:0) (molar ratio 1:4:2). Unlike the previous results using, a lysophospatidylglycerol containing composition containing curcumin, the a lysophospatidylcholine containing composition containing curcumin showed phase transitions at 26.35 and 152.86 degrees C., indicating that the composition was not a eutectic.

What is claimed:
1. A composition for solubilizing an agent, the composition comprising:
a lysophosphatidyl compound of the general formula IJ, a monoglyceride of the general formula IV and a free fatty acid of the general formula V:

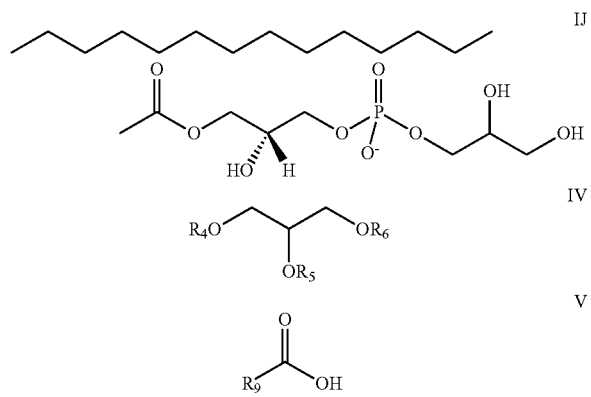

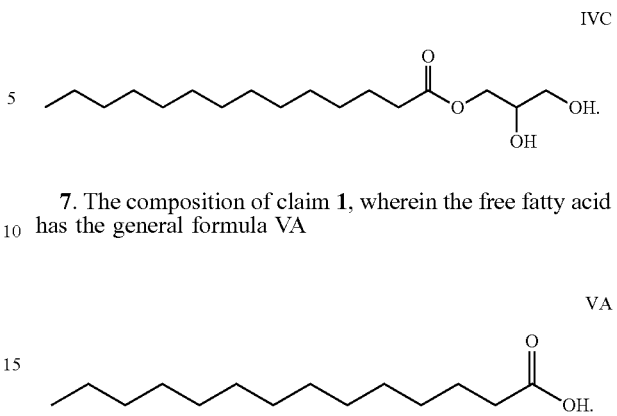

wherein,
one of $R_4$, $R_5$ and $R_6$ is —C(O)—$R_7$ and the remaining of $R_4$, $R_5$ and $R_6$ are each independently selected from H or $R_8$;
$R_7$ and $R_9$ are each independently a saturated or unsaturated carbon chain from 1 to 21 carbons in length; and
$R_8$ is saturated or unsaturated carbon chain from 1 to 10 carbons in length.

2. The composition of claim 1 further comprising the agent.

3. The composition of claim 1, wherein $R_7$ and $R_9$ are each independently a saturated carbon chain from 13 to 21 carbons in length.

4. The composition of claim 1, wherein $R_7$ and $R_9$ are each independently a saturated carbon chain from 6 to 12 carbons in length.

5. The composition of claim 1, wherein the monoglyceride has the general formula IVA or IVB and $R_7$ is a saturated carbon chain from 13 to 21 carbons in length:

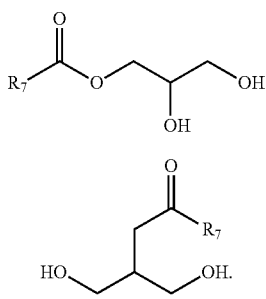

6. The composition of claim 1, wherein the monoglyceride has the general formula IVC 7. The composition of claim 1, wherein the free fatty acid has the general formula VA

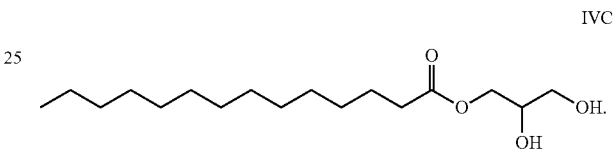

8. The composition of claim 1, wherein R9 is a saturated carbon chain from 13 to 15 carbons in length and the monoglyceride has the general formula IVC

IVC

9. The composition of claim 1, wherein the free fatty acid and monoglyceride are present in the composition in a molar ratio of between 2:1 and 1:2.

10. The composition of claim 1, wherein the free fatty acid and the monoglyceride comprise from about 70 mole percent to 99 mole percent of the composition, with the lysophosphatidyl compound comprising from about 30 mole percent to 1 mole percent of the composition, wherein the mole percentage values are expressed with regard to the lysophosphatidyl compound, the monoglyceride and the free fatty acid of the composition.

11. The composition of claim 1, wherein the ratios of the components of the composition are 1:4:2, 1:3:3, 2:4:2, or 1:2:4 mole percent lysophosphatidyl compound:monoglyceride:free fatty acid.

12. The composition of claim 1 further comprising the agent, wherein the composition forms a eutectic.

13. The composition of claim 12, wherein the agent is present at molar concentration of 1:1 or less with respect to the lysophosphatidyl compound.

14. The composition of claim 1, wherein the composition forms a eutectic.

15. A composition for solubilizing an agent, the composition comprising: a lysophosphatidyl compound of the general formula IJ, a monoglyceride of the general formula IVC and a free fatty acid of the general formula VA:

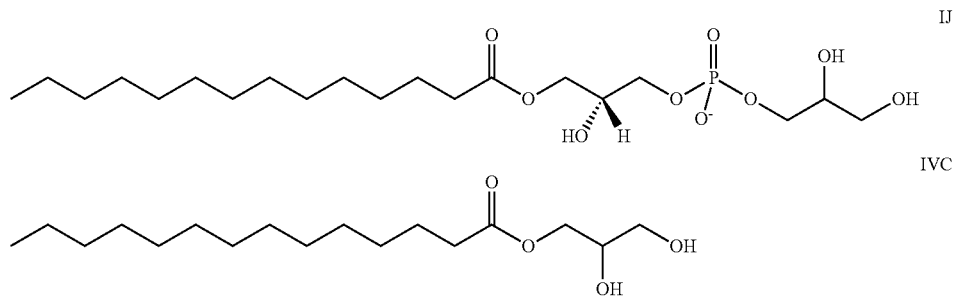

-continued

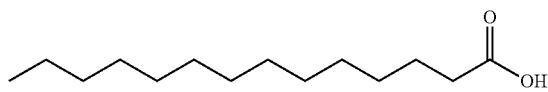

VA wherein the free fatty acid and monoglyceride are present in the composition in a molar ratio of between 2:1 and 1:2 and the free fatty acid and the monoglyceride comprise from about 70 mole percent to 99 mole percent of the composition, with the lysophosphatidyl compound comprising from about 30 mole percent to 1 mole percent of the composition, wherein the mole percentage values are expressed with regard to the lysophosphatidyl compound, the monoglyceride and the free fatty acid of the composition.

16. The composition of claim 15, wherein the ratios of the components of the composition are 1:4:2, 1:3:3, 2:4:2, or 1:2:4 mole percent lysophosphatidyl compound:monoglyceride:free fatty acid.

17. The composition of claim 15 further comprising the agent.

18. The composition of claim 15 further comprising the agent, wherein the composition forms a eutectic.

19. The composition of claim 18, wherein the agent is present at molar concentration of 1:1 or less with respect to the lysophosphatidyl compound.

20. The composition of claim 15, wherein the composition forms a eutectic.

* * * * *